United States Patent
Weng et al.

(10) Patent No.: US 9,682,063 B2
(45) Date of Patent: Jun. 20, 2017

(54) HCD FORMULATION FOR CANCER TREATMENT

(71) Applicant: National Dong Hwa University, Hualien (TW)

(72) Inventors: Ching-Feng Weng, Hualien (TW); Yi-Chen Chia, Hualien (TW); Chia-Hung Lee, Hualien (TW); T. Varadharajan, Hualien (TW)

(73) Assignee: National Dong Hwa University, Shoufeng Hualien (TW)

( * ) Notice: Subject to any disclaimer, the term of this patent is extended or adjusted under 35 U.S.C. 154(b) by 0 days.

(21) Appl. No.: 14/631,767

(22) Filed: Feb. 25, 2015

(65) Prior Publication Data

US 2016/0243236 A1 Aug. 25, 2016

(51) Int. Cl.
| | |
|---|---|
| *A61K 47/02* | (2006.01) |
| *A61K 31/365* | (2006.01) |
| *A61K 9/00* | (2006.01) |
| *A61K 9/51* | (2006.01) |

(52) U.S. Cl.
CPC .......... *A61K 31/365* (2013.01); *A61K 9/0019* (2013.01); *A61K 9/5115* (2013.01); *A61K 9/5138* (2013.01)

(58) Field of Classification Search
CPC A61K 49/0093; A61K 49/183; A61K 9/5115; B82Y 5/00; Y10T 428/2982
See application file for complete search history.

(56) References Cited

FOREIGN PATENT DOCUMENTS

CN 103505730 * 1/2014 ........... A61K 31/704

OTHER PUBLICATIONS

Kuthati (Journal of Nanoscience and Nanotechnology vol. 13, 2399-2430, 2013).*
Zhang et al. (Jornal of Controlled Release 145 (2010) 257-263).*
Lee et al. ( J. Phy. Chem C 2009, 113, 16058-16069).*
Lin et al. (Life Sciences 89 (2011) 886-895).*
Lipinski CA, "Drug-like properties and the causes of poor solubility and poor permeability", Journal of pharmacological and toxicological methods, 2000;44:235-49.
Merisko-Liversidge EM, "Drug nanoparticles: formulating poorly water-soluble compounds", Toxicol Pathol. 2008;36:43-8.
Zhang Y, "Inclusion of the poorly water-soluble drug simvastatin in mesocellular foam nanoparticles: drug loading and release properties", International journal of pharmaceutics. 2011;410:118-24.
Van Speybroeck M, et al., "Enhanced absorption of the poorly soluble drug fenofibrate by tuning its release rate from ordered mesoporous silica", European journal of pharmaceutical sciences : official journal of the European Federation for Pharmaceutical Sciences. 2010;41:623-30.
Thomas MJ, et al. "Inclusion of poorly soluble drugs in highly ordered mesoporous silica nanoparticles", International journal of pharmaceutics. 2010;387:272-7.
Lu J,"Mesoporous silica nanoparticles as a delivery system for hydrophobic anticancer drugs" Small. 2007;3:1341-6.
Chang FR, et al., "Anti-inflammatory and cytotoxic diterpenes from formosan *Polyalthia longifolia* var. *pendula*," Planta medica. 2006;72:1344-7.
Lin YH, et al. "16-hydroxycleroda-3,13-dien-15,16-olide regulates the expression of histone-modifying enzymes PRC2 complex and induces apoptosis in CML K562 cells", Life Sci. 2011;89:886-95.
Thiyagarajan V, "A novel inhibitor, 16-hydroxy-cleroda-3,13-dien-16,15-olide, blocks the autophosphorylation site of focal adhesion kinase (Y397) by molecular docking", Biochim Biophys Acta. 2013;1830:4091-101.
Reagan-Shaw S, Nihal et al., "Dose translation from animal to human studies revisited", FASEB J. 2007;22(3):659-61.
Jia Shen et al., "The use of hollow mesoporous silica nanospheres to encapsulate bortezomib and improve efficacy for non-small cell lung cancer therapy", Biomaterials, 2014; 35 (1), 316-326.
Rujia Zou et al., "Cu2-xSE@mSiO2-PEG core-shell nanoparticles: a low-toxic and efficient difunctional nanoplatform for chemo-photothermal . . . ", Nanoscale No. 6, 2014; 4361-4370.

* cited by examiner

*Primary Examiner* — Anna Falkowitz
(74) *Attorney, Agent, or Firm* — Haverstock & Owens LLP

(57) ABSTRACT

The present invention provides a novel formulation for cancer treatment and a method for enhancing the HCD's efficacy in cancer treatment. Specifically, the present invention provides copper-modified silica nanoparticles loaded with HCD, which exhibits better efficacy than some conventional anticancer drugs.

9 Claims, 8 Drawing Sheets

(A)

(B)

(C)

(D)

HCD FORMULATION FOR CANCER TREATMENT

BACKGROUND

Technical Field

The present disclosure relates to a formulation for cancer treatment; especially, to a formulation of HCD for cancer treatment.

Description of Related Art

A poorly water soluble drug candidate encountered in drug discovery causes increasing problems of poor and bioavailability. It is estimated that nearly 70% of new chemical entities are poorly soluble in aqueous medium. Besides, approximately 40% of currently marketed oral drugs are considered practically insoluble in water.

Among a variety of drug delivery systems, mesoporous silica nanoparticles (MSNs) has been several attractive features for use in the delivery of water insoluble drugs. MSNs have brought new possibilities to this burgeoning area of research field of Drug delivery. Different types of mesoporous materials with various pore sizes, pore structures, and surface functionality were designed for the drug formulations which can enhance absorption of the poorly soluble drug and provide sustained release.

16-Hydroxycleroda-3,13-dien-15,16-olide (HCD), extracted from the bark of *P. longifolia* exhibits strong anti-inflammatory activities and also regulates the expression of histone modifying enzymes PRC2 complex and induces apoptosis in CML K562 cells as well as potential in cancer treatment. However, because of its poor water solubility, the clinical application of HCD in cancer treatment is not ideal.

In light of the foregoing, a novel formulation for better exhibiting HCD's efficacy in cancer treatment is highly valued in the field.

SUMMARY

One of the objects of the present invention is to provide a novel formulation for cancer treatment.

Another object of the present invention is to provide a method for enhancing the efficacy of 16-hydroxy-cleroda-3,13-dine-15,16-olide (HCD) in cancer treatment.

In order to achieve the aforesaid objects, the present invention provides a formulation for cancer treatment, comprising: a copper-modified silica nanoparticle; and a pharmaceutically acceptable carrier. Preferably, said copper-modified silica nanoparticle is loaded with 16-hydroxy-cleroda-3,13-dine-15,16-olide (HCD).

The present invention also provides a method for enhancing the efficacy of 16-hydroxy-cleroda-3,13-dine-15,16-olide (HCD) for cancer treatment, comprising: loading said HCD to a copper-modified silica nanoparticle to obtain a copper-modified silica nanoparticle loaded with HCD.

Preferably, said silica nanoparticle is a mesoporous silica nanoparticle.

Preferably, said copper-modified silica nanoparticle loaded with HCD has a surface area less than 500 m$^2$/g.

Preferably, said copper-modified silica nanoparticle loaded with HCD has a pore volume less than 1.10 cm$^3$/g.

Preferably, said copper is modified with said silica nanoparticle via co-condensation of copper ions and a silica precursor (TEOS) through covalent bonding.

Preferably, said silica nanoparticle is loaded with said HCD via coordinate covalent bonding.

Preferably, said copper-modified silica nanoparticle loaded with HCD was further coated with a polymer with carboxylic functional groups.

Preferably, said polymer is a methacrylic acid and methyl methacrylate copolymer, polyvinyl acetate phthalate, a poly (ethylene glycol) triblock and diblock copolymer, or a combination thereof.

Preferably, said formulation has an effective amount of 0.25 to 2 mg/kg body weight/day.

Preferably, said pharmaceutically acceptable carrier is water, phosphate buffered saline, alcohol, glycerol, chitosan, alginate, chondroitin, Vitamin E, mineral oil, dimethyl sulfoxide (DMSO), or a combination thereof.

Preferably, said cancer is gliomas.

To sum up, the present invention shows a perfect match of HCD and Cu-modified silica nanoparticles in cancer treatment. Specifically, HCD loaded with said Cu-modified silica nanoparticles exhibits better efficacy in cancer treatment. Therefore, the clinical value for HCD's application in cancer treatment is moved further by the present invention.

DETAILED DESCRIPTION

Figure 1:
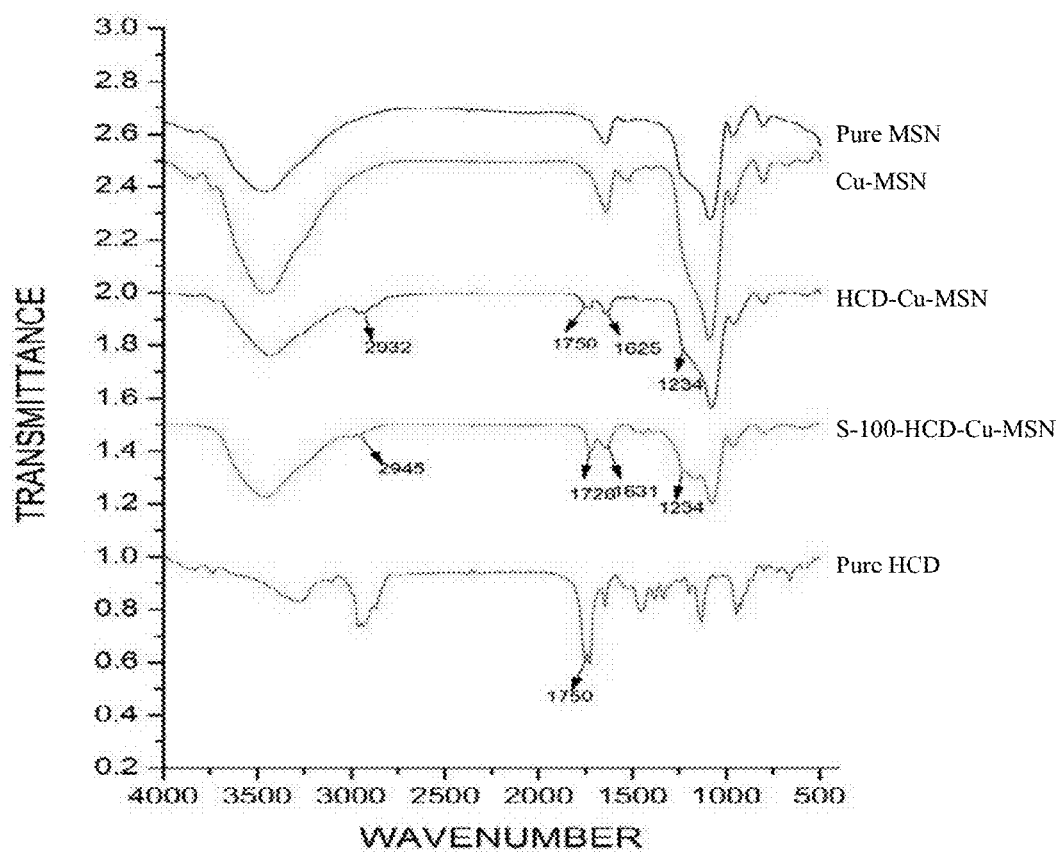
FIG. 1 shows the FT-IR spectra of the samples made in the Example 1 of the present invention.

In this study, 16-Hydroxycleroda-3,13-dien-15,16-olide (HCD), a natural anticancer drug, was selected for its delivery and protection by Cu-MSNs. MSNs were synthesized along with copper, characterized, and then loaded with HCD in order to increase its antitumor properties.

The term "treatment or treating" herein is referred to control or reduce the size of the tumor, prevent or limit the metastasis of the cancer cells, or a combination thereof. The term "effective amount" herein is referred to as an amount of the active ingredient that is sufficient to perform the aforesaid efficacies of treatment.

The term "pure" of "pure MSN" and "pure HCD" is to describe the MSN or HCD mentioned was used without being modified, loaded or coating with other materials but not to limit its purity from the perspective of analytical chemistry.

Said effective amount can be obtained from clinical trial, animal model, or in vitro cell culture data. It is known in the field that the effective amount obtained from animal model or in vitro cell culture data can be calculated into the effective amount suitable for human use. For instance, as reported by Reagan-Shaw et al., 2008, "μg/ml" (effective amount based on in vitro cell culture experiments)="mg/kg body weight/day" (effective amount for mouse). Furthermore, the effective amount for mouse can be further modified based on the fact that the metabolism rate of mice is 6 times faster compared to human.

Said pharmaceutically acceptable carrier in the present invention includes but not limited to water, phosphate buffered saline, alcohol, glycerol, chitosan, alginate, chondroitin, Vitamin E, mineral oil, dimethyl sulfoxide (DMSO), or a combination thereof. Generally, the pharmaceutically acceptable carrier can be chosen based on the desired administration route, components of the drug, treatment strategies, or purposes to be met.

The first aspect of the present invention provides a formulation for cancer treatment, comprising: a copper-modified silica nanoparticle; and a pharmaceutically acceptable carrier. The researches of the present invention surprisingly found that the copper-modified silica nanoparticle itself exhibited reliable efficacy in cancer treatment. Nevertheless, in a preferable embodiment of the present invention, said copper-modified silica nanoparticle is loaded with 16-hydroxy-cleroda-3,13-dine-15,16-olide (HCD).

The second aspect of the present invention provides a method for enhancing the efficacy of HCD for cancer treatment, comprising: loading said HCD to a copper-modified silica nanoparticle to obtain a copper-modified silica nanoparticle loaded with HCD.

In an alternative embodiment of the present invention, the silica nanoparticle used in the present invention is a mesoporous silica nanoparticle. In a preferable embodiment, the copper-modified silica nanoparticle loaded with HCD has a surface area less than 500 $m^2/g$. In a preferable embodiment, the copper-modified silica nanoparticle loaded with HCD has a pore volume less than 1.10 $cm^3/g$.

In a preferable embodiment of the present invention, the bonding relationship between the components of the present structure of copper-modified silica nanoparticle loaded with HCD is: said copper is modified with said silica nanoparticle via coordinate covalent bonding, and/or silica nanoparticle is loaded with said HCD via coordinate covalent bonding.

In a preferable embodiment of the present invention, said copper-modified silica nanoparticle loaded with HCD was further coated with a polymer with carboxylic functional groups. In an alternative embodiment of the present invention said polymer was coated with said copper-modified silica nanoparticle loaded with HCD via a coulomb electrostatic force between said carboxylic functional groups of said polymer and said copper. Said polymer includes but not limited to a methacrylic acid and methyl methacrylate copolymer, polyvinyl acetate phthalate, a poly(ethylene glycol) triblock and diblock copolymer, or a combination thereof. Commercial products including but not limited: Eudragit L100, S100, L-30D, FS-30D, L-100-55, HPMC55, can be used in the present invention.

Example 1: Preparation of the Present Formulation

In this example, a specific example of the present formulation was prepared. The 16-hydroxy-cleroda-3,13-dine-16, 15-olide (HCD) used in this example was obtained from Professor Yi-Chen Chia (Department of Food Science & Technology, Tajen University, Taiwan). Eudragit (S100) was purchased from Evonik industries. The preparation was summarized in the following paragraphs.

Preparation of Cu-Mesoporous Silica (Cu-MSN)

Cetrimonium bromide (0.58 g) was dissolved in $NH_4OH$ (0.51 M, 300 mL) at 40° C. and 5.0 g of structural swelling agent (n-octane) was then added and allowed to stir for 1 hour. To this 43.9 mg of $Cu(NO_3)_2.3H_2O$ (silica is 33 times higher than copper) was then added allowed to stir for 1 hour. After stirring, 5 mL of 0.2 M TEOS (tetraethoxysilane; in ethanol) was then added with vigorous stirring. After the solution was stirred for 5 hours, 5 mL of 0.2 M trimethylammonium silane (ethanol) was added and stirred for 5 min. Further, 5 mL of 1.0 M TEOS (ethanol) was added with vigorous stirring for another 2 h. The solution was aged at 40° C. for 20 hours. Samples were collected by centrifuging at 12000 rpm for 20 min, washed, and re-dispersed in deionized water and ethanol three times. The solid products were obtained by centrifugation and the surfactant templates were removed by extraction in 0.3 gm ammonium nitrate (ethanol) at 65° C. for 24 h. Further, the products were collected and washed with 20 mL ethanol three times.

Preparation of HCD loaded Cu-Mesoporous silica (HCD-Cu-MSN)

HCD (100 mg) was dissolved in 5 mL of ethanol (99.95%), Cu-MSN (100 mg) was then added to the HCD solution. The solution was then stirred at room temperature for 24 hours. Then, the product was collected by centrifugation of the solution at 12000 rpm for 20 min to remove free HCD.

Preparation of Eudragit S100 Coated HCD Loaded Cu-Mesoporous Silica (S100-HCD-Cu-MSN)

As prepared HCD-Cu-MSN was coated with Eudragit® co-polymer S100 for sustain drug release. A known weight (100 mg) of HCD-Cu-MSN was added to the solution in which Eudragit co-polymer S100 dispersed in 5% of ethanol and water in 20:1. The solution was then stirred at room temperature for 2 h. Then, it was allowed to centrifuge at 12000 rpm for 20 min to remove uncoated S100. Samples were allowed to dry and were subjected to various characterizations.

Example 2: Characterization of the Samples Made in Example 1

In this example, the pure MSN, Cu-MSN, HCD-Cu-MSN, and S100-HCD-Cu-MSN used or prepared in the Example 1 were characterized.
[Size and Zeta Potential]
The particle size and size distribution were measured by dynamic light scattering (DLS) and Zeta-potentials (Malvern Nano-HT Zetasizer) in de-ionized water with pH 7.4. All the DLS measurements were carried out at 25° C. and an angle detection of 90°. All the measurements were performed in triplicate.

The results (Table 1) showed that the nanoparticle size of 186.95-0.55 nm for pure MSN, 219.25±0.35 nm for Cu-MSN, 347.95±0.75 nm for HCD loaded Cu-MSN and 514.35±4.65 nm for S100 coated HCD-Cu-MSN with surface charge of −34.60±0.64 mV, −35.53±0.44 mV, −41.13±1.34 mV, and −43.60±0.37 mV respectively. While not wishing to be bound by theory, the increase in nanoparticle size and significant decrease in Zeta potential may be attributed to the presence of HCD loaded on Cu-MSN and S100 coated over the surface of drug loaded nanoparticles.

TABLE 1

Particle size and zeta potential of pure MSN, Cu-MSN, HCD-Cu-MSN and S100-HCD-Cu-MSN

| Sample | Particle size (nm) | Zeta potential (mV) |
|---|---|---|
| Pure MSN | 186.95 ± 0.55 | −34.60 ± 0.64 |
| Cu-MSN | 219.25 ± 0.35 | −35.53 ± 0.44 |
| HCD-Cu-MSN | 347.95 ± 0.75 | −41.13 ± 1.34 |
| S100-HCD-Cu-MSN | 514.35 ± 4.65 | −43.60 ± 0.37 |

All the data was measured at pH 7.4 (Double distilled water). Values are shown has mean ± SD, n = 3

[Analysis to the Structure of the Samples]

The following assays, including Fourier transform infrared spectroscopy (FT-IR), Thermo-gravimetric analysis (TGA), Brunauer-Emmett-Teller assay (BET), and Powder X-ray Diffraction (P-xrd), were conducted to confirm and analyzed the structure of the samples made in the Example 1.

1. FT-IR

To characterize the chemical bonds and surface organic groups within the samples of Example 1 as well as the post-synthesis modifications and conjugations thereof, a FT-IR spectroscopy (BRUKER ALPHA SPECTROMETER) was conducted. The experiment protocol was referred to the general procedure in the field. Briefly, the samples were finely grounded and dispersed in to KBr powder, respectively. The IR spectra, in absorbance mode, were obtained over the spectra region 400-4000 $cm^{-1}$.

The result of FT-IR was showed in FIG. 1. The FT-IR spectra of MSN reflected only the surface silanol groups and low frequency silica vibrations along with broad band (3100-3700 $cm^{-1}$) from the O—H stretch of the absorbed molecular $H_2O$. Like pure MSN and Cu-MSN, the FT-IR spectra of HCD-Cu-MSN exhibited an absorption band at 1720 $cm^{-1}$ corresponding to the carboxyl group (range 1700-1800 $cm^{-1}$). The 1720 $cm^{-1}$ absorption band confirmed the presence of carboxyl groups on the surface of the MSN moiety. The spectra of HCD-Cu-MSN also displayed the C=O stretch modes at or near 1234 $cm^{-1}$. Besides, the bands around 1625 and 2932 $cm^{-1}$ were attributed to C=C and C—H stretches of HCD moiety.

A sharp absorption band at 1150 $cm^{-1}$ for both the copper and HCD loaded MSNs (that is, Cu-MSN and HCD-Cu-MSN) confirms the intact silica ($SiO_2$) framework, even after functionalization of the MSN with copper. The presence of an absorption band at 1728 $cm^{-1}$ in the case of S100 polymer coated MSNs (that is, S100-HCD-Cu-MSN) along with all the above mentioned absorption bands unequivocally established the presence of Eudragit S100 polymer on the surface of the MSNs.

2. TGA

A Thermo-gravimetric analysis (TGA) was conducted to investigate the physical condition and composition of pure MSN, Cu-MSN, HCD-Cu-MSN, S100-HCD-Cu-MSN, and pure HCD. Briefly, the samples were heated from 25 to 800° C. at a heating rate of 20° C./min under dry nitrogen purge at a flow rate of 20 ml/min. Temperatures were recorded on TGA Q50 V 20.13 Build 39 (Universal V4.5A TA instruments).

Figure 2:
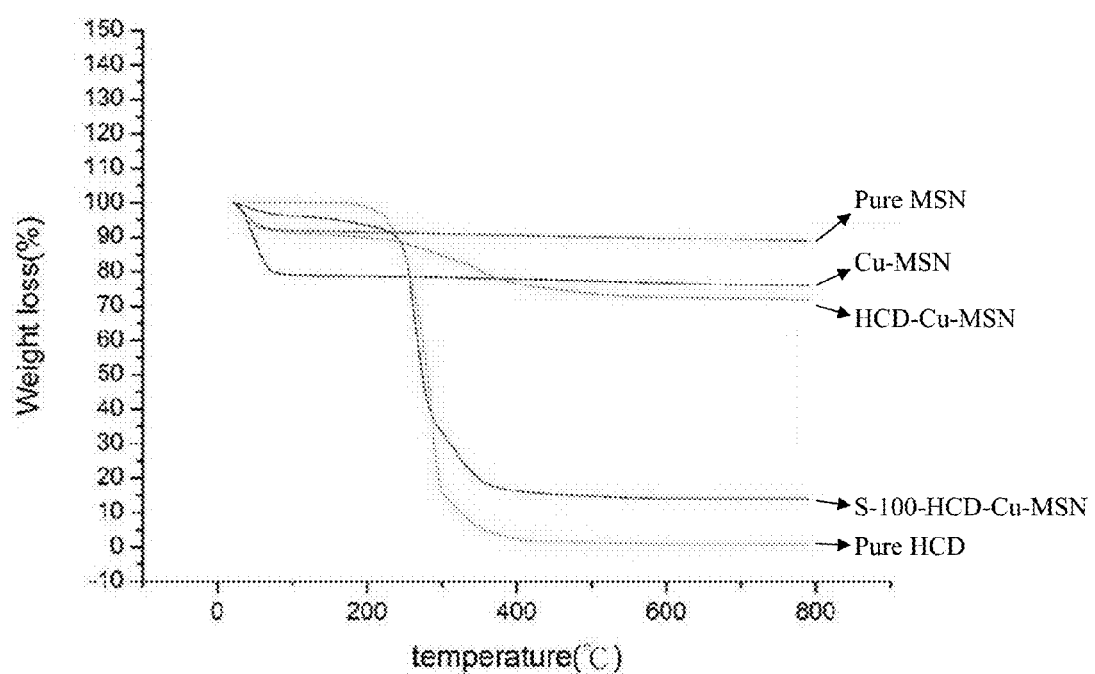
FIG. 2 shows the data of the thermo-gravimetric analysis (TGA) conducted in Example 2 of the present invention.

The results were shown in FIG. 2. For all of these samples, a slight weight loss was observed around 100° C., which is ascribed to residual water. There was only a very negligible weight loss can be observed in the pure MSN nanoparticles in between 200 and 600° C., which can be correlated to the condensation reaction between the Si—OH groups. The weight loss of copper functionalized MSN (Cu-MSN) was considerably less than that of pure MSN samples indicating the non-degradable nature and high loading of copper in the MSN channels.

The pure HCD was also examined by the TGA. Its weight loss pattern clearly showed degradation of drug at 285° C.; whereas Cu-MSN showed a weight loss at 346° C. due to the non-degradability of metal ions further confirming the loading of drug in to the mesoporous. In contrast, HCD loaded MSN (HCD-Cu-MSN) showed sharp weigh loss peak at 346° C. which indicate the decomposition of HCD drug molecules loaded in the Cu-MSN. Further coating of S100 over the nanoparticles resulted in high weight loss at 266° C. which confirms the high coating of S100 polymer over the synthesized nanoconjugates.

3. BET

The samples (pure MSN, Cu-MSN, HCD-Cu-MSN, S100-HCD-Cu-MSN, and pure HCD) were subjected to verify the surface morphology by Brunauer-Emmett-Teller (BET) studies, which disclosed surface area by N2 adsorption-desorption isotherms at 77 K on a Micrometric ASAP 2010 apparatus. The samples were degassed at $10^{-3}$ Torr at 100° C. for 16 h prior to the adsorption experiment.

Figure 3:
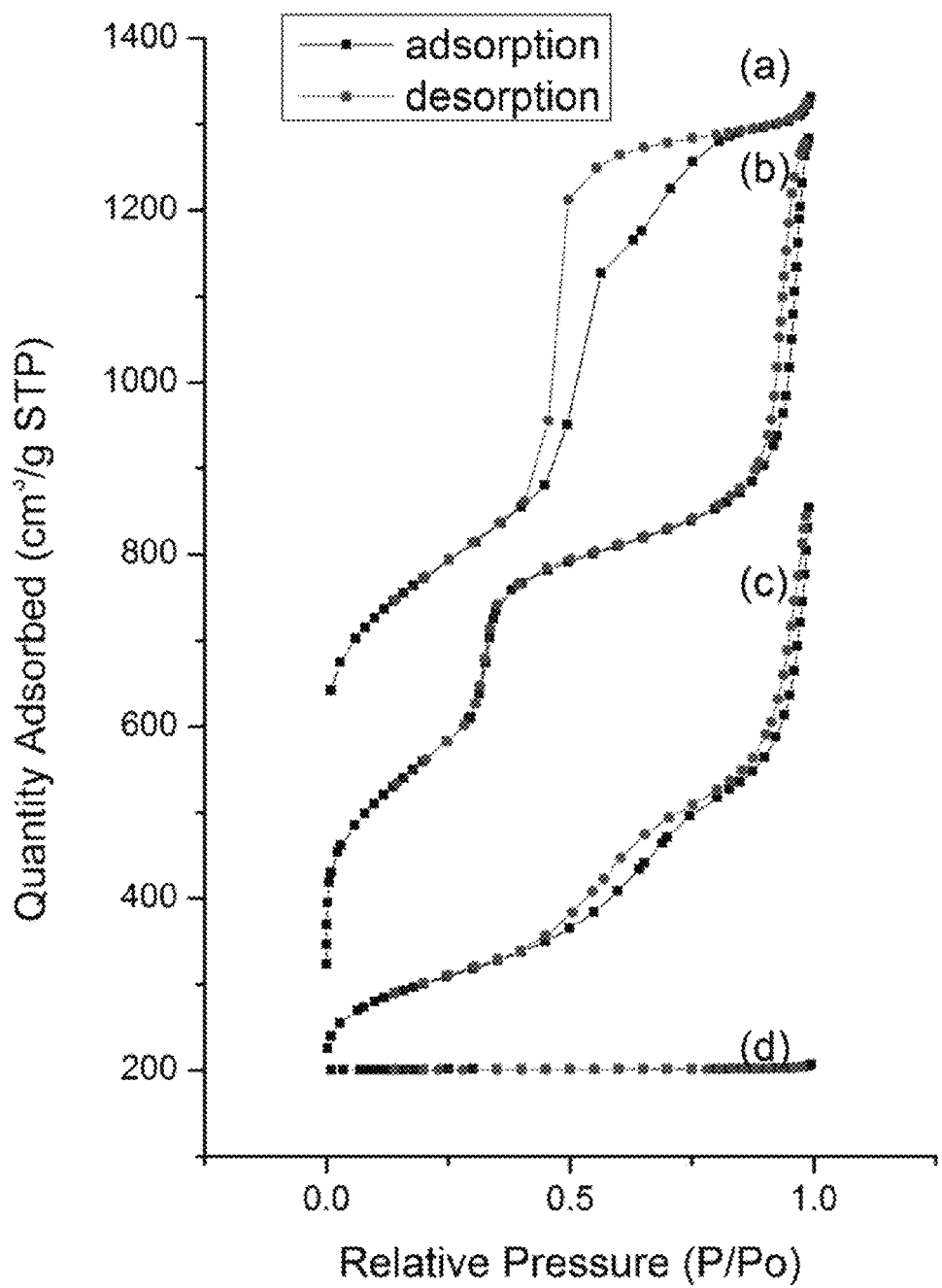
FIG. 3 shows the results of the Brunauer-Emmett-Teller (BET) conducted in Example 2 of the present invention. (a) MSN (b) Cu-MSN (c) HCD-Cu-MSN (d) S100-HCD Cu-MSN.

The results were shown in FIG. 3 and Table 2.

TABLE 2

Surface area, pore volume and pore size of pure MSN, Cu-MSN, HCD-Cu-MSN and S100-HCD-Cu-MSN

| Nanoparticle | Surface Area ($m^2/g$) | Pore Volume ($cm^3/g$) | Pore Size (Å) |
|---|---|---|---|
| P-MSN | 1174.8 | 1.52 | 48.9 |
| Cu-MSN | 981.8 | 1.29 | 43.9 |
| HCD-Cu-MSN | 380.4 | 1.01 | ND |
| S100-HCD-Cu-MSN | 3.0 | 0.01 | ND |

ND—not determined

There was a significant decrease in surface area and pore volume of nanoparticles with each post modification in comparison to the pure MSN samples. Surface area of pure MSN sample decreased from 1174.8 $m^2/g$ to 981.8 $m^2/g$ up on modification with copper. Further with the modification of HCD and S100, the surface areas have fallen down to 380.4 $m^2/g$ and 2.9 $m^2/g$ respectively, which suggested the high loading of HCD in the mesoporous channels of MSN.

Simultaneously, the pore volumes decreased from 1.52 $cm^3/g$ to 1.29 $cm^3/g$ and 1.01 $cm^3/g$ after modification of particles with copper and HCD. The pore volume drastically reduced to 0.01 $cm^3/g$ after coating the nanoconjugates with S100 confirming the high loading capacity of drug and polymer in and on the surface of nanoparticles. Thus, the modification of the copper, the conjugation of the HCD, and the coating of S100 polymer were confirmed.

Figure 4:
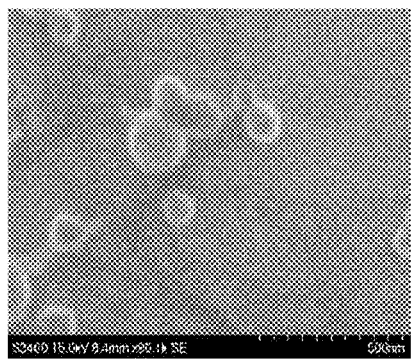
FIG. 4 shows the images of scanning electron microscopy of (A) MSN, (B) Cu-MSN, (C) HCD-Cu-MSN, and (D) S100-HCD-Cu-MSN.
Figure 4:
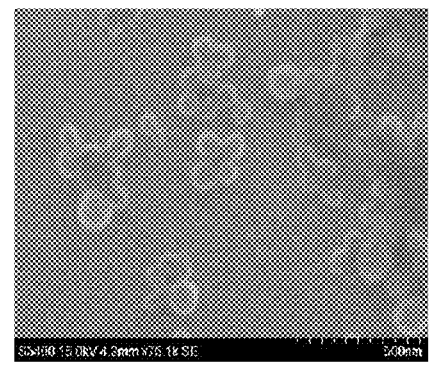
Figure 4:
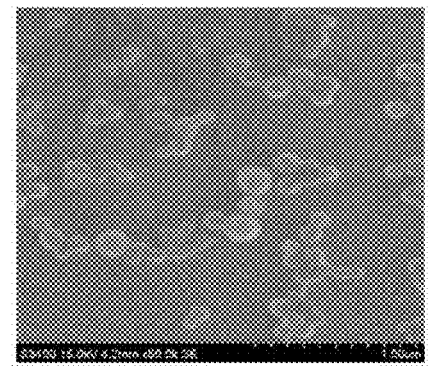
Figure 4:
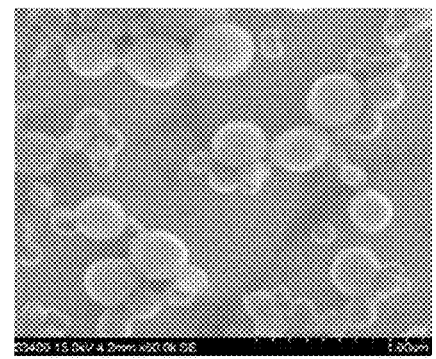

The pore size distribution showed a slight decrease from 4.9 nm to 4.4 nm upon loading the MSN particles with copper, which confirmed the loading of drug and the successful coating of polymer layer over the surface of MSN. Furthermore, morphology of MSN, Cu-MSN, HCD-Cu-MSN and S100-HCD-Cu-MSN were also determined by scanning electron microscopy (FIG. 4).

4. P-Xrd

P-xrd pattern of MSN, Cu-MSN, HCD-Cu-MSN and S100-HCD-Cu-MSN was carried out using X-ray diffractometer (XRD D8 Advanced, Bruker). The diffraction angle (2θ) was recorded from 0° to 80° with a scanning speed of 3°/min. CuKα-radiation was used as X-ray source at 40 Kv and 40 mA.

Figure 5:
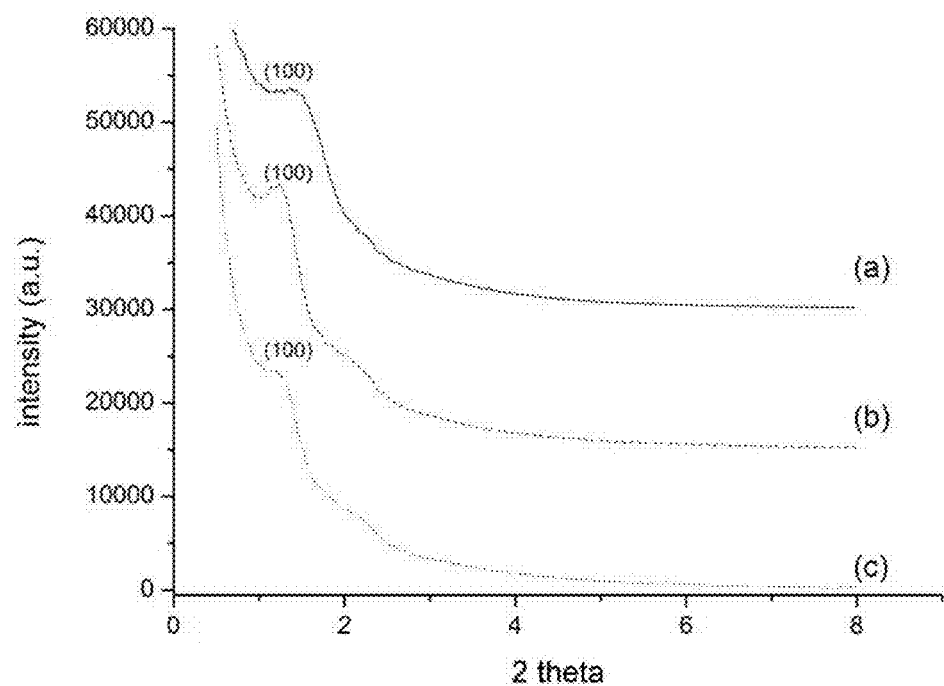
FIG. 5 shows the P-xrd pattern of Cu-MSN, HCD-Cu-MSN and S100-HCD-Cu-MSN. (a) Cu-MSN (b) HCD-Cu-MSN (c) S100-HCD-Cu-MSN.

The powder X-ray diffraction patterns for the Cu-MSN, HCD loaded Cu-MSN (HCD-Cu-MSN) and S100 coated HCD-Cu-MSN (S100-HCD-Cu-MSN), are shown in FIG. 5. The Cu-MSN showed a strong peak at 2θ=1.2 corresponds to the (100) diffraction peak of hexagonal lattice symmetry. Whereas, other samples showed decrease in intensity, this gradual decrease of d-spacing could be attributed to the concentration of unit cells upon surface functionalization and metal ions within the pores of MSN.

[Analysis to the Structure of the Samples]

An ideal drug carrier should have a high drug loading capacity. The drug loading percentage was calculated by the following equation:

$$\text{Drug Loading (\%)} = \frac{\left(\begin{array}{c}\text{Initial amount of} \\ \text{HCD used}\end{array}\right) - \left(\begin{array}{c}\text{Amount of HCD} \\ \text{in supernatant}\end{array}\right)}{\text{Amount of Cu-MSN used}}$$

Our results showed that HCD loaded in to the Cu-MSN effectively achieving a loading percentage of 18±0.8% (further repeated trials concluded that the loading percentage was less than 50%; data not shown). HCD was analyzed with a UV-vis absorption spectrophotometer at 224 nm.

The controlled and sustained release of drugs from a carrier system is an important property for its clinical application in the biomedicine for cancer treatment. In vitro release experiments were performed at pH values of 7.4, 5 and 1.2 using citrate sodium hypophosphate buffer. For each release study, 1 mL of buffer solution was added to 5 mg of HCD-Cu-MSN/S100 coated HCD-Cu-MSN and maintained at 37° C., while being stirred at 100 rpm 48 hours. Release medium was removed for analysis at specific time intervals by centrifuging at 12000 rpm for 10 min. The amount of released HCD was analyzed with a UV-vis absorption spectrophotometer at 224 nm.

Figure 6:
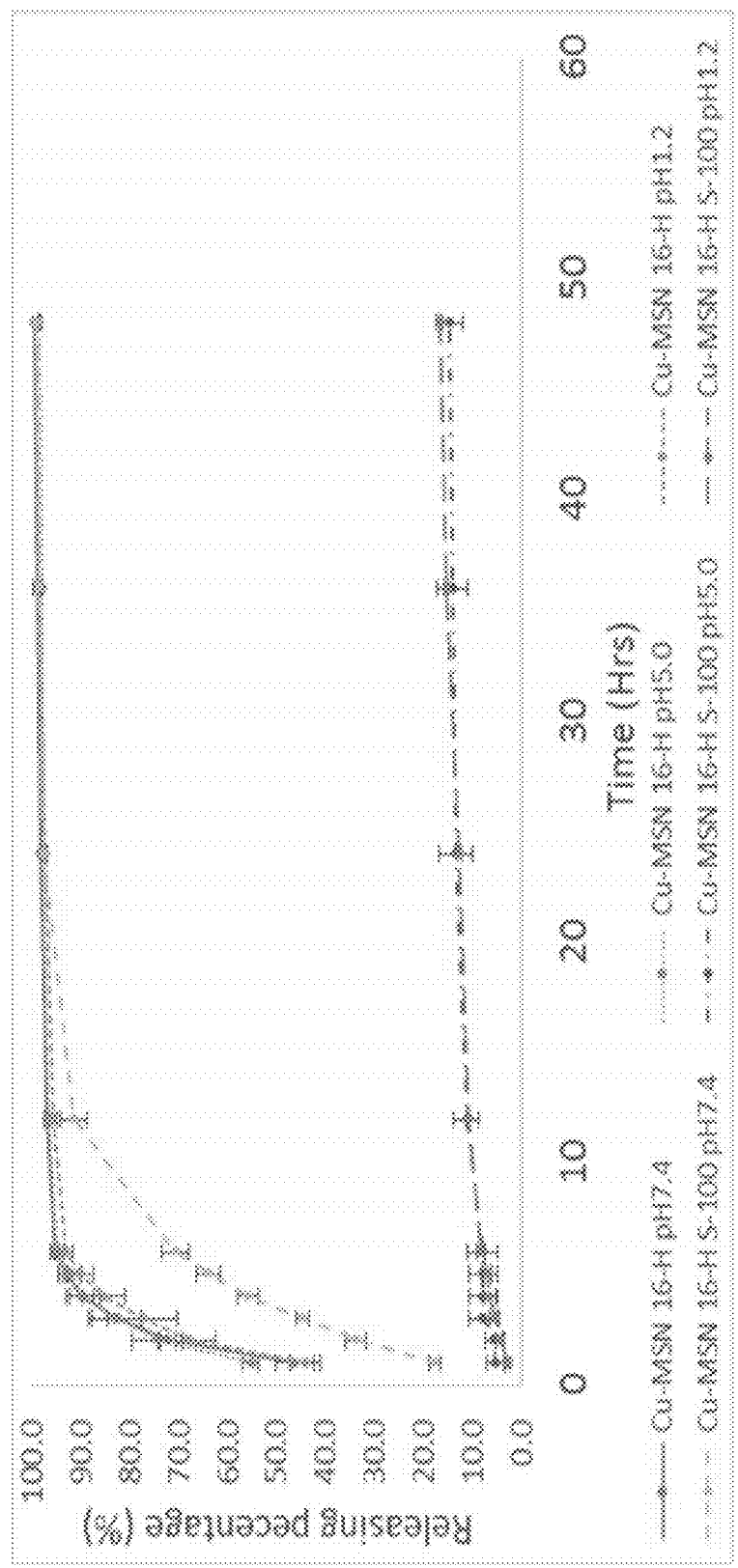
FIG. 6 shows Release Profiles of HCD from non-coated HCD-Cu-MSN (HCD-Cu-MSN) and S100 coated HCD-Cu-MSN (S100-HCD-Cu-MSN) at pH values of 7.4, 5 and 1.2, respectively.

FIG. 6 demonstrated that the non coated HCD-Cu-MSN were shown uncontrolled drug leaching at pH 7.4, 5 and 1.2, but enteric (S100) coated sample showed a sustained release profile and prevented the drug leaching ability in the pH 1.2 and 5 even after 48 hours as compared to non coated samples. The presence of carboxylate groups of Eudragit should facilitate a strong interaction between the monolayer of the polymer with the MSN layer. This result indicates that Eudragite S100 coated nanoparticles were pH dependent.

Example 3: Inhibitory Efficacy of the Samples Made in Example 1 to Tumor Cells In this example, the in vitro cytotoxicity to tumor cell line of the samples was examined by MTT assay and then the inhibitory efficacy thereof to tumor cells was tested. Statistical comparisons of the results were made using analysis of variance (ANOVA). Data were expressed as the means±SD. Significant differences (*$p<0.05$), ($p<0.01$), and (*$p<0.001$) between the means of control and the treatment were analyzed by the Tukey test.

1. Cytotoxicity

Rat glioma C6 cell lines were used for the experiments. Cell line was cultured in DMEM supplemented with 15% horse serum, 2.5% FBS and 1% antibiotics (100 U/mL of penicillin and 100 μg/mL of streptomycin) at 37° C. in a humidified atmosphere of 5% $CO_2$.

The cells were seeded in 96-well plates at a density of $1 \times 10^4$ cells/well. Cells were treated with different concentrations (100 μL) of pure MSN, Cu-MSN, HCD-Cu-MSN and free HCD for 4 h. After 4 h incubation, Further 100 μL media contain 30% horse serum and 5% FBS media was added and incubated for 24 h in order to prevent the cell starvation. After 24 h incubation, the media was replaced with 20 μL of MTT reagent (5 mg/mL) and incubated in 5% $CO_2$ at 37° C. for 4 h. DMSO (100 μL) was added to each well for 15 min, and the cell viability was determined by measuring the absorbance at 570 nm using a plate-reader (Thermo Labsystems, Opsys MR, ThermoFisher Scientific, Waltham, Mass., USA).

Figure 7:
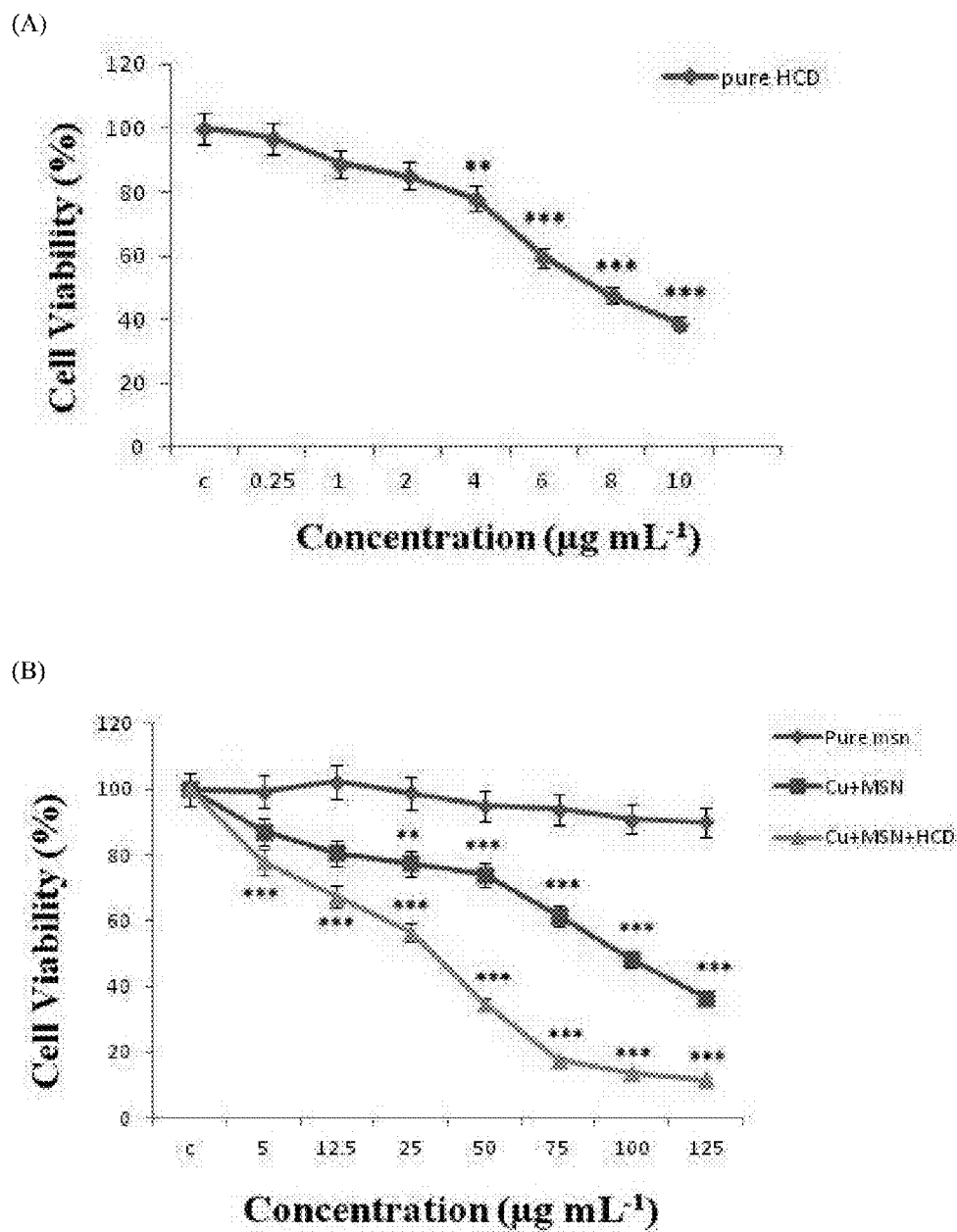
FIG. 7 shows the results of MTT assay (C6 cells) conducted in Example 3. (A) free HCD; (B) pure MSN, Cu-MSN, S100-HCD-Cu-MSN, respectively.

The results were showed in FIG. 7. A significant decrease in cell viability was observed following an increased concentration of HCD-Cu-MSN treatment. Cu-MSN showed an $IC_{50}$ value at 100 μg, free HCD showed an $IC_{50}$ value at 8 g (FIG. 7A) and HCD-Cu-MSN at 25 μg (FIG. 7B). Cells treated with pure MSN showed no cytotoxicity effect even at higher concentrations. The IC50 values of HCD-Cu-MSN were larger than that of free HCD. The reason might be attributed to different uptake pathways of free drugs and drug loaded nanoparticles, and the controlled release manner of drug loaded nanoparticles.

Specifically, in cell culture medium, most of the free drugs might be quickly display their effects after being transported in to a cell via passive diffusion. However, drug loaded nanoparticles were mainly up taken via endocytosis process and exhibited antitumor activity after drug molecules from nanoparticles were released. Besides, the data surprisingly shows that Cu-MSN without loading with HCD exhibited significant inhibitory efficacy to C6 cells.

2. In Vivo Tumor Growth Inhibition

After the in vitro effectiveness of the HCD-Cu-MSN had been confirmed, the in vivo efficacy was tested in a xenograft C6 rat glioma bearing mouse model.

Six-week-old athymic male nude mice were purchased from LASCO (Charles River technology, Taipei, Taiwan). All animal experiments were performed in accordance with the "Guide for the care and use of Laboratory animals" of National Dong-Hwa University (Hualien, Taiwan). A total of $5 \times 10^5$ C6 cells were injected subcutaneously on the back of nude mice. When the tumor volume reached an average volume of about 200 $mm^3$, mice were randomly divided in to four groups: 5 mice received intraperitoneal injection of normal saline as control (n=5) and 5 received intraperitoneal administration of HCD (0.16 mg/kg body weight/day, n=5), and 5 received intraperitoneal injection of cisplatin (0.06 mg/kg body weight/day, n=5) or S100-HCD-Cu-MSN (0.5 mg/kg body weight/day, n=5) was given orally (Cisplatin and S100-HCD-Cu-MSN was dissolved in saline) and once daily for 10 days. The mice were sacrificed and tumors were excised and weighed. Major organs such as liver, kidney, spleen, and tumor were subjected to histological analysis.

Figure 8:
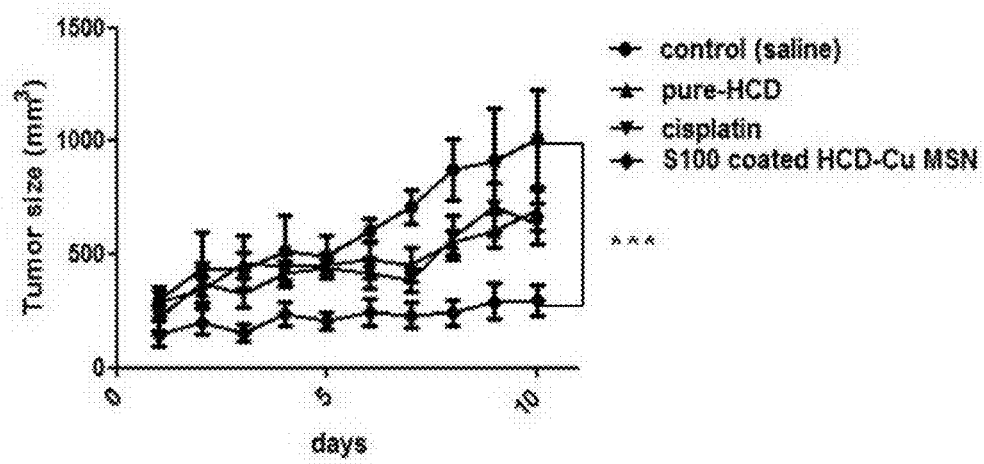
FIG. 8 shows the change of tumor size during the In vivo tumor growth inhibition experiment in Example 3 of the present invention.

As shown in FIG. 8, compared with saline treatment group, drug formulations showed better efficacy in inhibiting tumor growth. The drug loaded nanoparticle showed significant difference (**$p<0.01$) and better antitumor effect as compared with free drug and cisplatin, and no obvious tumor recrudescence during the complete treatment. Although not intend to be bonded by any theory, the high efficacy of drug loaded nanoparticle might be attributed to the enhanced nanoparticle stability during the blood circulation, efficient cellular uptake and synergistic effect of copper and HCD on tumor inhibition.

Figure 9:
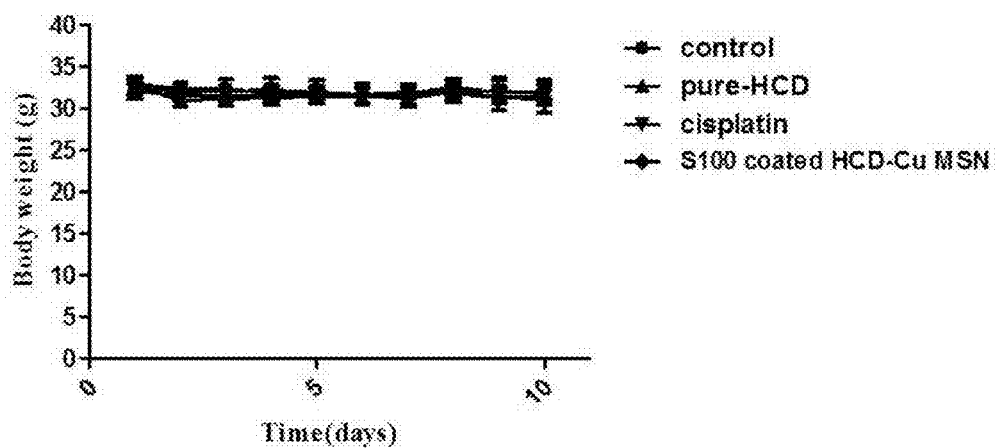
FIG. 9 shows the change of body weight during the In vivo tumor growth inhibition experiment in Example 3 of the present invention.

In addition, changes in mean body weight were also determined as a measure of drug induced toxicity. Treatments did not show visible toxicity, as a decrease in body weight was not observed in any group (FIG. 9).

In light of the foregoing, our results surprisingly showed that HCD-Cu-MSN has improved efficacy in cancer treatment via in vivo examination. Furthermore, our results also showed that Cu-MSN also exhibited significant efficacy in inhibiting tumor cell viability. That said, a novel synergistic effect provided by the present formulation of HCD-Cu-MSN was firstly proved by the present invention.

What is claimed is:

1. A formulation for gliomas treatment, comprising:
a copper-modified silica nanoparticle; and
a pharmaceutically acceptable carrier;
wherein said copper-modified silica nanoparticle is loaded with 16-hydroxy-cleroda-3,13-dine-15,16-olide (HCD);
wherein said silica nanoparticle is a mesoporous silica nanoparticle.

2. The formulation of claim 1, wherein said copper-modified silica nanoparticle loaded with HCD has a surface area less than 500 $m^2/g$.

3. The formulation of claim 1, wherein said copper-modified silica nanoparticle loaded with HCD has a pore volume less than 1.10 $cm^3/g$.

4. The formulation of claim 1, wherein said copper is modified with said silica nanoparticle via co-condensation of copper ions and silica precursor (TEOS).

5. The formulation of claim 1, wherein said silica nanoparticle is loaded with said HCD via coordinate covalent bonding.

6. The formulation of claim 1, wherein said copper-modified silica nanoparticle loaded with HCD was further coated with a polymer with carboxylic functional groups.

7. The formulation of claim 6, wherein said polymer is a methacrylic acid and methyl methacrylate copolymer, polyvinyl acetate phthalate, a poly(ethylene glycol) triblock and diblock copolymer, or a combination thereof.

8. The formulation of claim 6, having an effective amount of 0.25 to 2 mg/kg body weight/day.

9. The formulation of claim 1, wherein said pharmaceutically acceptable carrier is water, phosphate buffered saline, alcohol, glycerol, chitosan, alginate, chondroitin, Vitamin E, mineral oil, dimethyl sulfoxide (DMSO), or a combination thereof.

* * * * *

UNITED STATES PATENT AND TRADEMARK OFFICE
CERTIFICATE OF CORRECTION

PATENT NO. : 9,682,063 B2
APPLICATION NO. : 14/631767
DATED : June 20, 2017
INVENTOR(S) : Ching-Feng Weng et al.

It is certified that error appears in the above-identified patent and that said Letters Patent is hereby corrected as shown below:

Column 4 at Line 65; the amount "186.95-0.55 nm" should read -- 186.95 ± 0.55 nm --.

Column 8 at Lines 23-24; the amount "8 g" should read -- 8 µg --.

Signed and Sealed this
Twenty-fourth Day of April, 2018

Andrei Iancu
*Director of the United States Patent and Trademark Office*